(12) United States Patent
Misicka-Kęsik et al.

(10) Patent No.: US 10,301,352 B2
(45) Date of Patent: May 28, 2019

(54) PEPTIDOMIMETICS WITH ANTIANGIOGENIC ACTIVITY

(71) Applicant: UNIWERSYTET WARSZAWSKI, Warsaw (PL)

(72) Inventors: Aleksandra Misicka-Kęsik, Piastów (PL); Dagmara Tymecka, Warsaw (PL); Bartlomiej Fedorczyk, Warsaw (PL); Piotr Sosnowski, Czerwin (PL); Beata Wileńska, Piastów (PL); Ewa Witkowska, Zielonka (PL); Patrick Ladam, Esches (FR); Gerard Y. Perret, Boulogne-Billancour (FR); Anna Starzec, Warsaw (PL)

(73) Assignee: UNIWERSYTET WARSZAWSKI, Warsaw (PL)

( * ) Notice: Subject to any disclaimer, the term of this patent is extended or adjusted under 35 U.S.C. 154(b) by 0 days.

(21) Appl. No.: 14/913,380

(22) PCT Filed: Aug. 23, 2014

(86) PCT No.: PCT/PL2014/050051
§ 371 (c)(1),
(2) Date: Feb. 22, 2016

(87) PCT Pub. No.: WO2015/026251
PCT Pub. Date: Feb. 26, 2015

(65) Prior Publication Data
US 2016/0333047 A1 Nov. 17, 2016

(30) Foreign Application Priority Data
Aug. 23, 2013 (PL) .......................... 405129

(51) Int. Cl.
C07K 5/11 (2006.01)
C07K 5/02 (2006.01)
A61K 38/00 (2006.01)

(52) U.S. Cl.
CPC ............ *C07K 5/0215* (2013.01); *A61K 38/00* (2013.01)

(58) Field of Classification Search
None
See application file for complete search history.

(56) References Cited

FOREIGN PATENT DOCUMENTS

WO 99/47158 A2 9/1999

OTHER PUBLICATIONS

International Search Report and Written Opinion issued in corresponding International Patent Application No. PCT/PL2014/050051 dated Jan. 23, 2015 (8 pages).
Starzec et al., "Antiangiogenic and antitumor activities of peptide inhibiting the vascular endothelial growth factor binding to neuropilin-1," Life Sciences, vol. 79, 2006, pp. 2370-2381.

*Primary Examiner* — Karlheinz R. Skowronek
*Assistant Examiner* — Ronald T Niebauer
(74) *Attorney, Agent, or Firm* — Kilyk & Bowersox, P.L.L.C.

(57) ABSTRACT

We disclose novel peptidomimetics with antiangiogenic activity and their uses, particularly in the treatment of neoplasms and chronic inflammation (in particular of: rheumatoid arthritis, colitis), in eczema, diabetes, age-related macular degeneration (ARMD), nephropathy and neuropathy, in particular for use in the form of intravenous infusions or injections, or implants releasing the active ingredient.

8 Claims, 1 Drawing Sheet
Specification includes a Sequence Listing.

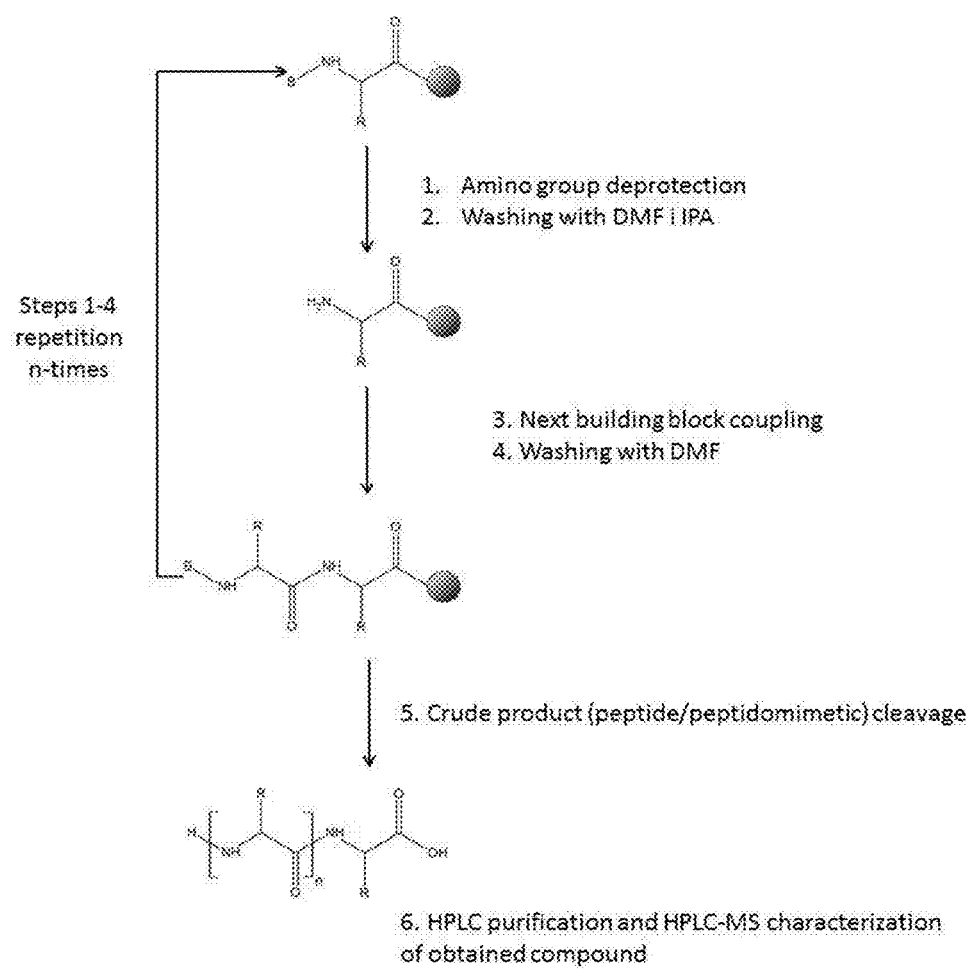

PEPTIDOMIMETICS WITH ANTIANGIOGENIC ACTIVITY

This application is a National Stage Application of PCT/PL2014/050051, filed Aug. 23, 2014, which claims priority to Polish Patent Application No. P405129, filed Aug. 23, 2013.

The subject of the present invention are novel peptidomimetics with antiangiogenic activity, a method of obtaining them, a pharmaceutical composition as well as their use, particularly in the treatment of neoplasms and chronic inflammation (in particular of: rheumatoid arthritis, colitis), in eczema, diabetes, age-related macular degeneration (ARMD), nephropathy and neuropathy, in particular in the form of intravenous infusions or injections, or implants.

Angiogenesis is a biological process that is based on the creation of new blood vessels by endothelial cells, within an existing circulatory system. The generation of capillaries can occur both in physiological and pathological conditions. Excessive angiogenesis occurs at sites of inflammation, diseases or neoplasms. Examples of diseases where excessive angiogenic activity has been observed are endometriosis, eczema, ulceration as well as rheumatoid arthritis. During the formation of neoplasms, angiogenesis is necessary for the growth of tumours beyond 2-3 mm, as well as for metastases.

The most important proangiogenic factor that stimulates angiogenesis is a group of proteins jointly called Vascular Endothelial Growth Factor. The strongest effect is induced by $VEGF_{165}$, which binds to its receptors and signals endothelial cells to proliferate angiogenetically. The most important $VEGF_{165}$ receptor is VEGF Receptor 2, a tyrosine kinase, which in the presence of a blood protein called neuropilin-1 (NRP-1) forms a strong bond with $VEGF_{165}$ and causes a strong proangiogenic signal to be transmitted. For this reason, substances that block the formation of the $VEGF_{165}$/VEGFR2/NRP-1 complex may be potential anti-tumour drugs. (Cook, K M and Figg, W D. Angiogenesis inhibitors: current strategies and future prospects. Cancer J. Clin. 60, 222, 2010, Folkman, J. Tumor angiogenesis; therapeutic implications. N. Engl. J. Med. 285, 1182, 1976, Samant, R S. and Shevde, L A Recent advances in antiangiogenic therapy of cancer. Oncotarget 2, 122, 2011)

So far, both in vitro, and in vivo research has shown the efficacy of angiogenesis blocking using inhibitory peptides of the $VEGF_{165}$/VEGFR2/NRP-1 system (Starzec A., Vasy R., Martin A., Lecouvey M., Di Benedetto M., Crepin M., Perret GY Antiangiogenic and antitumour activities of peptide inhibiting the vascular endothelial growth factor binding to neuropilinl, Life Sci. 70, 2370, 2006).

There is still an extant need for compounds which could inhibit angiogenesis.

The subject of the present invention are novel peptidomimetics defined by the general formula:

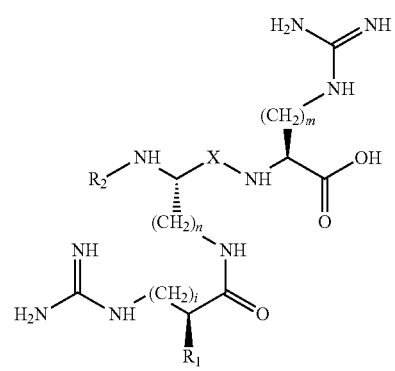

where:
i is an integer from 1 to 9
n is an integer from 1 to 4
m is an integer 3 or 4
$R_1$ denotes: —H, —$NH_2$, —NH—CO—$CH_3$, —NH-Cbz, or —NH-Fmoc,
where: Fmoc=a 9-fluorenylmethoxycarbonyl group, Cbz=a benzyloxycarbonyl
$R_2$ denotes: —H, —CO—$CH_3$, -Fmoc, or -Cbz.
X denotes one of the following molecular fragments from a) to e):

a)
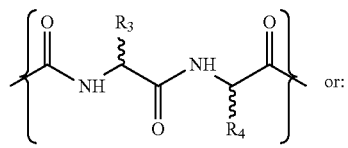 or:

b)
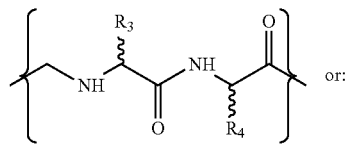 or:

c)
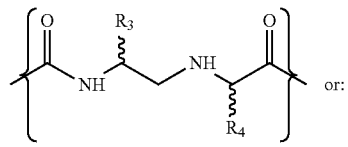 or:

d)
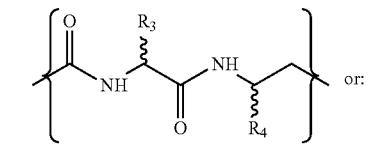 or:

where:
$R_3$ and $R_4$ denote independently of one another a group selected from a set the side chains of: glycine, alanine, 2,3-diaminopropionic acid, 2,4-diaminobutanoic acid, ornithine, lysine, or proline conked to the carbon atom in an S or R configuration
or:
e) —CO—NH—$(CH_2)_k$—CO—NH—, where k constitutes an integer in the range of 2-7,
or their derivatives containing a reduced peptide bond,
or their pharmaceutically acceptable salts.

Preferably, the subject of the present invention are compounds defined by the formula:

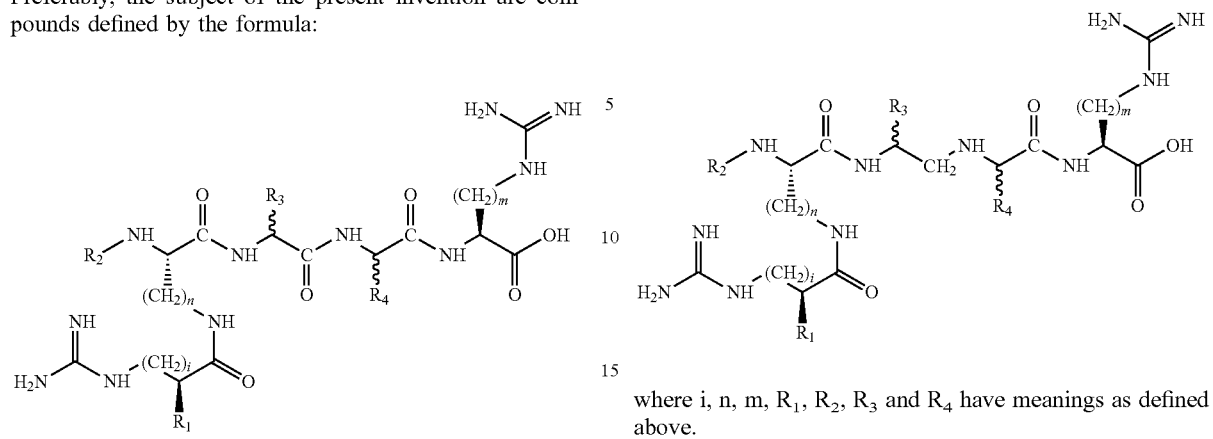

where i, n, m, $R_1$, $R_2$, $R_3$ and $R_4$ have meanings as defined above.

Preferably in compounds according to the present invention, at least one of the peptide bonds denoted as A, B or C in the formula below may be reduced:

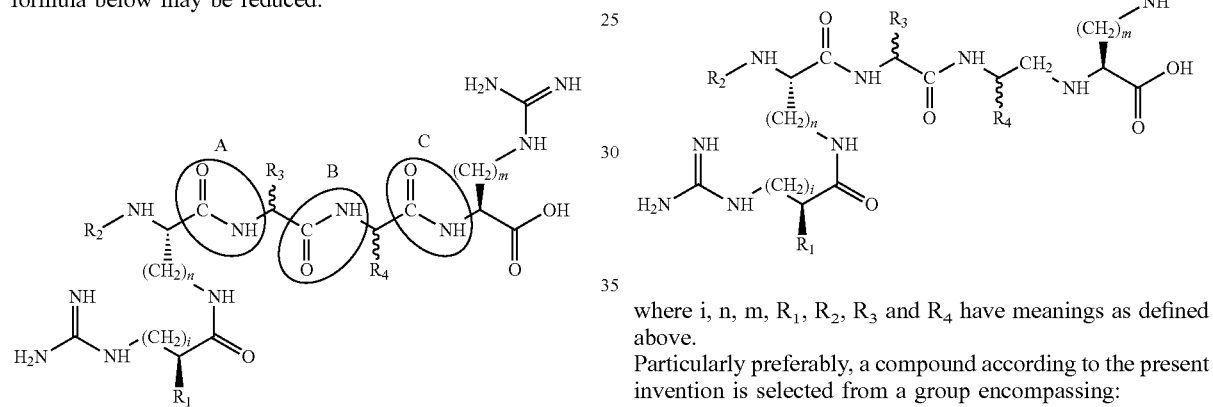

wherein i, n, m, $R_1$, $R_2$, $R_3$ and $R_4$ have meanings as defined above.

Preferably, the subject of the present invention are compounds with reduced peptide bond A defined by the formula:

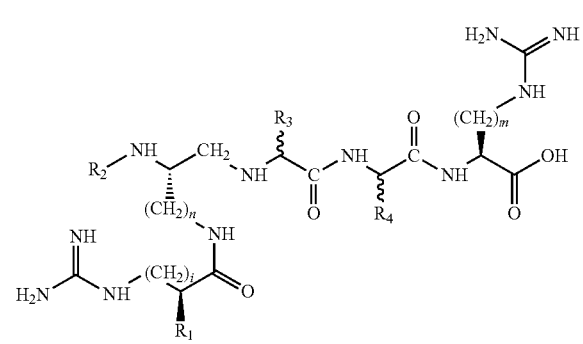

where i, n, m, $R_1$, $R_2$, $R_3$ and $R_4$ have meanings as defined above.

Equally preferably, the subject of the present invention are compounds with reduced peptide bond B defined by the formula:

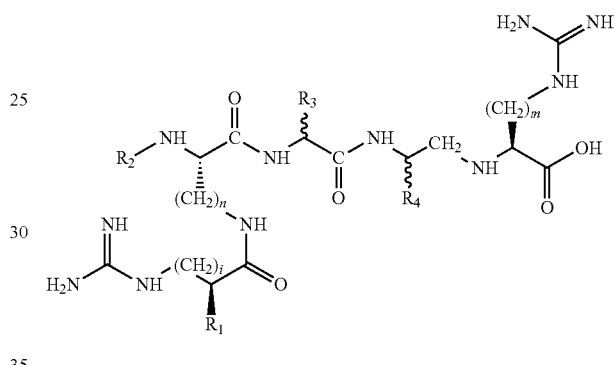

where i, n, m, $R_1$, $R_2$, $R_3$ and $R_4$ have meanings as defined above.

Preferably, the subject of the present invention are compounds with reduced peptide bond C defined by the formula:

where i, n, m, $R_1$, $R_2$, $R_3$ and $R_4$ have meanings as defined above.

Particularly preferably, a compound according to the present invention is selected from a group encompassing:
Lys(hArg)-Pro-Dab-Arg,
Lys(hArg)-Dap-Pro-Arg,
Lys(hArg)-Dab-Pro-Arg,
Lys(hArg)-Ala-Ala-Arg,
Lys(hArg)-Ala-Pro-Arg,
Lys(hArg)-Pro-Ala-Arg,
Lys(11-Aun(g))-Pro-Dab-Arg,
Lys(7-Ahp(g))-Pro-Dab-Arg,
Lys(hArg)-Pro-Dap-Arg,
Lys(hArg)-Pro-Pro-Arg,
Lys(Dab(g))-Pro-Dab-Arg,
Dab(hArg)-Pro-Dab-Arg,
Orn(Arg)-Pro-Dab-Arg,
Orn(hArg)-Pro-Dab-Arg,
Lys(Arg)-Pro-Dab-Arg or their pharmaceutically admissible salts, where (g) denotes a guanidyl group, 11-Aun denotes 11-aminoundecanoic acid residue, 7-Ahp denotes a 7-aminoheptanoic acid residue.

Preferably, compounds according to the present invention may be in the form of salts, hydrates or other pharmaceutically permissible complexes. Pharmaceutically permissible salts encompass addition salts with inorganic acids, such as hydrochloric, hydrobromic, sulphuric, phosphoric or similar acid, or with organic acids such as acetic, propionic, lactic, maleic, fumaric, citric, tartaric or similar acid.

The invention also relates to a pharmaceutical composition for the treatment of neoplasms and inflammatory diseases, containing as its active ingredient novel peptidomimetics with antiangiogenic activity, with the above defined general formula 1 or their pharmaceutically acceptable salts as well as a pharmaceutically acceptable carrier.

Prior to administration, the compounds are prepared preferably in the form of appropriate pharmaceutical preparations using known additives, such as a pharmaceutically acceptable carrier, diluent or ancillary substance.

Compounds according to the present invention may be administered as intravenous infusions or subcutaneous implants, or implants into tissues warranting the best accessibility of the released novel antiangiogenic peptidomimetic to its target sites.

Compounds according to the present invention may be administered as the sole active ingredient of a pharmaceutical composition or as a component of a multi-drug pharmaceutical composition designed for use in therapy, particularly antiangiogenic and/or antitumour therapy.

EXAMPLE 1. SYNTHESIS OF THE COMPOUNDS OF THE PRESENT INVENTION

FIG. 1 illustrates the general preparation of compounds of the present invention.

Peptidomimetics of the present invention may be obtained by using the well-known procedures of the Solid Phase Peptide Synthesis (SPPS). The functional groups of the side-chains of the building blocks should be protected with orthogonal protecting groups that are eliminated under acidic or basic conditions. All the protecting groups used should be stable under the conditions of peptide bond formation or formation of its isoster, while their removal should not result in the destruction of the growing peptide chain or racemization of any of the chiral centers. The preferred N-α-protecting groups are: 9-fluorenylmethyloxycarbonyl group (Fmoc) or tert-butyloxycarbonyl group. Other protecting groups proposed for the protection of functional groups in the side chain building blocks are: 2,2,4,6,7-pentamethyl-dihydrobenzofurane-5-sulfonyl group (Pbf), 2,2,5,7,8-pentamethylchromane-6-sulfonyl group (Pmc), 4-methoxy-2,3,6-trimethylbenzylsulfonyl group (Mtr), p-toluenesulfonyl group (Tos), Boc, Fmoc, 4-methyltrityl group (Mtt), 4-methoxytrityl group (Mmt), benzyloxycarbonyl group (Cbz, Z), 1-(4,4-Dimethyl-2,6-dioxocyclohex-1-ylidene)-3-methyl-butyl group (ivDde), 2-chlorobenzyloxycarbonyl group (2-Cl—Z). For the synthesis of peptidomimetics, all C-terminal amino acids are attached to a polymeric support which is chemically inert and insoluble in the reaction media used. The 4-(hydroxymethyl)phenoxymethyl linker which is directly attached to a polystyrene base matrix (Wang resin) is a preferred resin for the peptide synthesis in the Fmoc strategy. For the Boc strategy the chloromethylpolystyrene with 1% of divinylbenzene is preferred as a polymer matrix. Peptide bonds were obtained by using the following coupling reagents: N,N'-dicyclohexylcarbodiimide with addition of hydroxybenzotriazole (HOBt), N,N'-diisopropylcarbodiimide with addition of HOBt, N,N,N',N'-tetramethyl-O-(1H-benzotriazol-1-yl)uronium hexafluorophosphate (HBTU), N,N,N',N'-tetramethyl-O-(benzotriazol-1-yl)uronium tetrafluoroborate (TBTU), 1-[bis(dimethylamino)methylene]-1H-1,2,3-triazolo[4,5-b]pyridinium 3-oxid hexafluorophosphate (HATU), (1-cyano-2-ethoxy-2-oxo-ethylidenaminooxy)dimethyl-amino-morpholino-carbenium hexafluorophosphate (COMU), benzotriazol-1-yloxy-tris(dimethylamino)phosphonium hexafluorophosphate (BOP).

The final step of the synthesis, is the cleavage of the peptide from the resin and, depending on the case strategy, it is preferred to use: liquid hydrofluoric acid (HF) with the addition of anisole or a mixture of trifluoroacetic acid/water/triisopropylsilane (95:2.5:2.5 v/v/v). The crude products may be purified using high performance liquid chromatography on a reverse phase column packed with a C-12 or C-18 gradient of 0%-15% (B) over 30 minutes, where phase (A) is 0.05% TFA in H2O and the phase (B) is 0.05% TFA in ACN. The products obtained can optionally be converted to a desired pharmaceutically acceptable salt using a conventional method.

EXAMPLE 2. A METHOD FOR THE SYNTHESIS OF COMPOUNDS OF FORMULA 1, WHERE X IS A FORMULA DESCRIBED IN SUBSECTION A

The procedure for the synthesis of this group of compounds of the present invention is discussed below. The peptide H-Lys(hArg)-Pro-Dab-Arg-COOH was chosen as the example:

160 mg of pre-loaded Fmoc-L-Arg(Pbf) WANG resin was mixed in 4 ml of the anhydrous N,N-dimethylformamide (DMF) for four hours. After that time, the resin was filtered off and then mixed in 6 ml of 20% (v/v) piperidine in DMF for 5 minutes, then the resin was filtered off and a fresh aliquot of 20% piperidine in DMF was added (6 ml) and stirred for another 20 minutes. The next step of the synthesis was the alternately washing of the resin with 6 mL of dry DMF and 6 ml of isopropanol (IPA) until neutral pH, usually three times for one minute each. At the end of this step of the synthesis, the resin was washed three times (for one minute) with a fresh portion of anhydrous DMF. After the wash sequence, for monitoring of the completion of the Fmoc cleavage, the colorimetric assay was made. Usually, for primary amines, this is the Kaiser test. For this purpose a few resin beads were placed in small test tube and few drops (equal volumes) of the three solutions [(A): 5 g of ninhydrin in 100 ml ethanol; (B): 80 g phenol in 20 ml of ethanol; (C) 2 ml 0.001 M aqueous KCN in 98 ml pyridine] were added. The test tube was placed in a water bath and heated for 5 minutes at 100° C. A positive Kaiser test result (deep blue color of resin and solution) was obtained which allowed us to proceed to the next step wherein 88 mg (0.2 mmol) of Fmoc-Dab(Boc)-OH, 64 mg (0.2 mmol) TBTU and 51 mL (0.3 mmol) DIPEA were dissolved in 5 ml of anhydrous DMF—to form the preactivation mixture. The preactivation mixture was stirred for 10 minutes and added to the resin and mixed for another 10 minutes, then additional 51 mL (0.3 mmol) of DIPEA was added and mixing was continued for another four hours. After this time the resin was filtered off and washed four times (1 minute) with a fresh portion (6 ml) of anhydrous DMF, and then again the Kaiser test was performed with negative result (which means the completion of the coupling reaction). Next, the resin was mixed in 6 ml of 20% (v/v) piperidine in DMF for 5 minutes, then the resin was filtered off and fresh aliquot of 20% piperidine in DMF was added (6 ml) and stirred for another 20 minutes. The further step of the synthesis was the alternately washing of the resin with 6 mL of dry DMF and 6 ml of isopropanol (IPA) until neutral pH, usually three times (DMF and IPA) for one minute each. At the end of this step of the synthesis, the resin was washed three times (for one minute) with a fresh portion of anhydrous DMF. After the wash sequence, for monitoring of the completion of the Fmoc cleavage, the Kaiser test was made. Also in this case, the positive result of Kaiser test was obtained which allowed to proceed to the next step wherein 67 mg (0.2 mmol) of Fmoc-Pro-OH, 64 mg (0.2 mmol) of TBTU and 51 mL (0.3 mmol) of DIPEA were dissolved in 5 ml of anhydrous DMF—to form the preactivation mixture. The preactivation mixture was stirred for 10 minutes and added to the resin and mixed for another 10 minutes, then additional 51 mL (0.3 mmol) of DIPEA was added and mixing was continued for another four hours. After this time, the resin was filtered off and washed four times (1 minute) with a fresh portion (6 ml) of anhydrous DMF, and then again the Kaiser test was performed. The result of Kaiser test was negative, which means the completion of the coupling reaction. Next, the resin was mixed in 6 ml of 20% (v/v) piperidine in DMF for 5 minutes, then the resin was filtered off and a fresh aliquot of 20% piperidine in DMF was added (6 ml) and stirred for another 20 minutes. The further step of the synthesis was the alternately washing of the resin with 6 mL of dry DMF and 6 ml of isopropanol (IPA) until neutral pH, usually three times (DMF and IPA) for one minute each. At the end of this step of the synthesis, the resin was washed three times (for one minute) with a fresh portion of anhydrous DMF. For monitoring of the completion of the Fmoc cleavage from proline residue the acetaldehyde/chloranil test was performed. For this purpose a few resin beads were placed in small test tube and few drops (equal volumes) of the two solutions [(A): 2% acetaldehyde in DMF; (B): 2% chloranil in DMF] were added. After a short mixing the mixture was left at room temperature for 5 minutes. After that time, the dark blue color of beads of resin indicated the completion of the Fmoc cleavage. In the next step of the synthesis, the preactivation mixture consist of the 94 mg (0.2 mmol) of Boc-Lys(Fmoc)-OH, 64 mg (0.2 mmol) of TBTU, 51 mL of DIPEA and dissolved in 5 mL of dry DMF was stirred for 10 minutes and added to the resin and mixed for another 10 minutes, then additional 51 mL (0.3 mmol) of DIPEA was added and mixing was continued for another four hours. After this time, the resin was filtered off and washed four times (1 minute) with a fresh portion (6 ml) of anhydrous DMF, and then again the acetaldehyde/chloranil test was performed. Lack of the color of beads indicated the completion of coupling reaction. Next, the resin was mixed in 6 ml of 20% (v/v) piperidine in DMF for 5 minutes, then the resin was filtered off and a fresh aliquot of 20% piperidine in DMF was added (6 ml) and stirred for another 20 minutes. The further step of the synthesis was the alternately washing of the resin with 6 mL of dry DMF and 6 ml of isopropanol (IPA) until neutral pH, usually three times (DMF and IPA) for one minute each. At the end of this step of the synthesis, the resin was washed three times (for one minute) with a fresh portion of dry DMF. For monitoring of the completion of the Fmoc cleavage, the Kaiser test was made. Also in this case, the positive result of Kaiser test was obtained which allowed to proceed to the next step wherein the 94 mg (0.2 mmol) of Boc-Lys(Fmoc)-OH, 64 mg (0.2 mmol) of TBTU and 51 mL of DIPEA were dissolved in 5 ml of anhydrous DMF—to form the preactivation mixture. The preactivation mixture was stirred for 10 minutes and added to the resin and mixed for another 10 minutes, then additional 51 mL (0.3 mmol) of DIPEA was added and mixing was continued for another four hours. After this time, the resin was filtered off and washed four times (1 minute) with a fresh portion (6 ml) of anhydrous DMF, and then again the Kaiser test was performed. The result of Kaiser test was negative, which means the completion of the coupling reaction. Next, the resin was mixed in 6 ml of 20% (v/v) piperidine in DMF for 5 minutes, then the resin was filtered off and a fresh aliquot of 20% piperidine in DMF was added (6 ml) and stirred for another 20 minutes. The further step of the synthesis was the alternately washing of the resin with 6 mL of dry DMF and 6 ml of isopropanol (IPA) until neutral pH, usually three times (DMF and IPA) for one minute each. At the end of this step of the synthesis, the resin was washed three times (for one minute) with a fresh portion of anhydrous DMF. For monitoring of the completion of the Fmoc cleavage from lysine residue the Kaiser test was performed. As usual, the deep blue color of resin and solution indicated that deprotection of amino group was completed. The final step of the synthesis was the introduction of the guanidino group into side chain of lysine to achieve the homo-arginine residue. For this purpose, 100 mg (0.5 mmol) of commercially available 1-amidino-3,5-dimethylpyrazole nitrate was dissolved in 5 ml of DMF and the pH of the solution was adjusted to 11 with DIPEA. The mixture was then added to peptidyl-resin and allowed to stir for 3 days. After this time, the resin was filtered off and washed three times (1 minute) with a fresh portion (6 ml) of anhydrous DMF, and then the Kaiser test was performed. The result of Kaiser test was negative, which means the completion of the guanidylation reaction. The next step of the synthesis was the washing of the peptidyl-resin with 5 mL of dry dichloromethane (DCM), 5 ml of methanol (MeOH) and 5 ml of diethyl ether ($Et_2O$), five times for one minute each and subsequently the peptidyl-resin was dried under vacuum. Complete acidolytic cleavage and deprotection was occurred after 5 hours of stirring the resin in a mixture of $TFA/TIS/H_2O$ in a ratio of 95:2.5:2.5 (v/v/v). Next the resin was filtered off and crude peptide was precipitated by adding the cleavage mixture dropwise into a large excess of the cold diethyl ether. Finally, the crude peptide was purified by semi-preparative high performance liquid chromatography (HPLC) using the C-12 reverse phase column. Elution was done by linear gradient 0%-15% (B) in 30 minutes where buffer (A) was 0.05% TFA in water and buffer (B) was 0.05% TFA in ACN.

We obtained a compound defined by the formula:

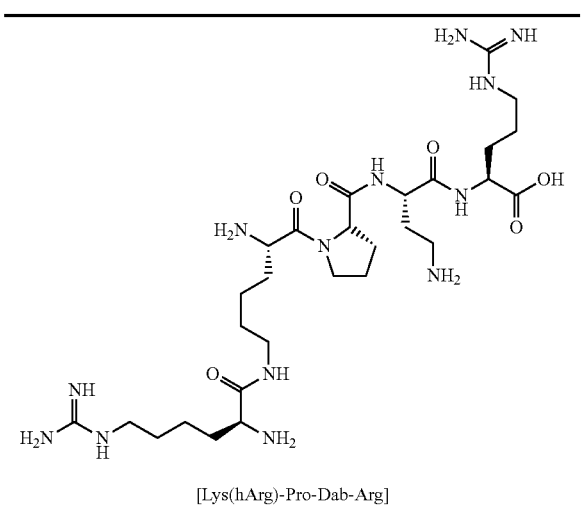

[Lys(hArg)-Pro-Dab-Arg]

| | Calculated MS | Found MS |
|---|---|---|
| $[M + H]^+$ | 670.45 | 670.05 |
| $[M + 2H]^{2+}$ | 335.73 | 335.60 |
| $[M + 3H]^{3+}$ | 224.15 | 223.95 |

HPLC: $t_R$=13.96 min in a linear gradient of 0%-15% (B) over 20 minutes, where phase (A) is 0.05% TFA in $H_2O$ and phase (B) is 0.05% TFA in ACN.

In an analogous fashion we can obtain other compounds according to the present invention that belong to the same group.

For example, by an analogous method we obtained Lys(hArg)-Dap-Pro-Arg defined by the formula:

[Lys(hArg)-Dap-Pro-Arg]

|  | Calculated MS | Found MS |
|---|---|---|
| $[M + H]^+$ | 656.43 | 656.00 |
| $[M + 2H]^{2+}$ | 328.72 | 328.60 |
| $[M + 3H]^{3+}$ | 219.48 | 219.45 |

HPLC: $t_R$=10.55 min in a linear gradient of 0%-15% (B) over 20 minutes, where phase (A) is 0.05% TFA in $H_2O$ and phase (B) is 0.05% TFA in ACN.

Likewise, also for example, by an analogous method we obtained Lys(hArg)-Dab-Pro-Arg defined by the formula:

[Lys(hArg)-Dab-Pro-Arg]

|  | Calculated MS | Found MS |
|---|---|---|
| $[M + H]^+$ | 670.45 | 670.00 |
| $[M + 2H]^{2+}$ | 335.73 | 335.60 |
| $[M + 3H]^{3+}$ | 224.15 | 224.15 |

HPLC: $t_R$=10.06 min in a linear gradient of 0%-15% (B) over 20 minutes, where phase (A) is 0.05% TFA in $H_2O$ and phase (B) is 0.05% TFA in ACN.

For example, by an analogous method we obtained peptidomimetics indicated in Table 1.

TABLE 1

Chemical properties of example compounds according to the present invention.

| Peptide formula | Calculated MS | Measured MS |
|---|---|---|
| Lys(hArg)-Ala-Ala-Arg | 615.40 $[M + H]^+$ | 615.00 $[M + H]^+$ |
|  | 308.21 $[M + 2H]^{2+}$ | 308.10 $[M + 2H]^{2+}$ |
| Lys(hArg)-Ala-Pro-Arg | 641.42 $[M + H]^+$ | 641.10 $[M + H]^+$ |
|  | 321.21 $[M + 2H]^{2+}$ | 321.15 $[M + 2H]^{2+}$ |
| Lys(hArg)-Pro-Ala-Arg | 641.42 $[M + H]^+$ | 641.10 $[M + H]^+$ |
|  | 321.21 $[M + 2H]^{2+}$ | 321.10 $[M + 2H]^{2+}$ |
|  | 214.48 $[M + 3H]^{3+}$ | 214.40 $[M + 3H]^{3+}$ |
| Lys(11-Aun(g))-Pro-Dab-Arg | 725.51 $[M + H]^+$ | 725.10 $[M + H]^+$ |
|  | 363.26 $[M + 2H]^{2+}$ | 363.25 $[M + 2H]^{2+}$ |
|  | 242.51 $[M + 3H]^{3+}$ | 242.40 $[M + 3H]^{3+}$ |
| Lys(7-Ahp(g))-Pro-Dab-Arg | 669.45 $[M + H]^+$ | 669.05 $[M + H]^+$ |
|  | 335.23 $[M + 2H]^{2+}$ | 335.10 $[M + 2H]^{2+}$ |
|  | 223.82 $[M + 3H]^{3+}$ | 223.75 $[M + 3H]^{3+}$ |
| Lys(hArg)-Pro-Dap-Arg | 656.43 $[M + H]^+$ | 656.05 $[M + H]^+$ |
|  | 328.72 $[M + 2H]^{2+}$ | 328.70 $[M + 2H]^{2+}$ |
| Lys(hArg)-Pro-Pro-Arg | 667.43 $[M + H]^+$ | 667.05 $[M + H]^+$ |
|  | 334.22 $[M + 2H]^{2+}$ | 334.20 $[M + 2H]^{2+}$ |
|  | 223.15 $[M + 3H]^{3+}$ | 223.10 $[M + 3H]^{3+}$ |
| Lys(Dab(g))-Pro-Dab-Arg | 642.41 $[M + H]^+$ | 642.05 $[M + H]^+$ |
|  | 321.71 $[M + 2H]^{2+}$ | 321.60 $[M + 2H]^{2+}$ |
| Dab(hArg)-Pro-Dab-Arg | 642.41 $[M + H]^+$ | 642.05 $[M + H]^+$ |
|  | 321.71 $[M + 2H]^{2+}$ | 321.55 $[M + 2H]^{2+}$ |
| Orn(Arg)-Pro-Dab-Arg | 642.41 $[M + H]^+$ | 641.95 $[M + H]^+$ |
|  | 321.71 $[M + 2H]^{2+}$ | 321.55 $[M + 2H]^{2+}$ |
| Orn(hArg)-Pro-Dab-Arg | 656.43 $[M + H]^+$ | 656.05 $[M + H]^+$ |
|  | 328.72 $[M + 2H]^{2+}$ | 328.60 $[M + 2H]^{2+}$ |
| Lys(Arg)-Pro-Dab-Arg | 656.43 $[M + H]^+$ | 656.10 $[M + H]^+$ |
|  | 328.72 $[M + 2H]^{2+}$ | 328.65 $[M + 2H]^{2+}$ |
|  | 219.48 $[M + 3H]^3$ | 219.40 $[M + 3H]^{3+}$ |

Where (g) denotes a guanidyl group, 11-Aun denotes 11-aminoundecanoic acid residue, 7-Ahp denotes a 7-aminoheptanoic acid residue.

The transformation of peptide bonds marked with A, B or C mentioned before, into reduced bonds might be achieved in a well known way, for instance, by the use of N-blocked amino aldehydes. Synthesis of N-Boc blocked amino aldehydes was carried out according to procedure described previously in literature: Fehrentz, J. A.; Castro, B. Synthesis 1983, 676-678, and then by reductive amination step described by Mi-Sun P., Hyun-Sik O., Hyeongjin C., Keun-Hyeung L. Tetrahedron Letters 2007, 1053-1057 have led to reduced peptide bond forming.

EXAMPLE 3. SYNTHESIS OF A COMPOUND WITH THE GENERAL STRUCTURE 1, WHERE X STANDS FOR ONE OF THE POSSIBLE VARIANTS DESCRIBED IN POINTS A, B OR C

General procedure for this compounds group according to the invention is discussed below as an exemplary synthesis of H-Lys(hArg)Ala[$CH_2$—NH]Arg-OH:

270 mg of Merrifield resin with arginine attached onto [Boc-Arg(Tos)-Merrifield] with loading 0.37 mmol/g was stirred for 30 minutes in 6 ml of methylene chloride (DCM). After that resin was filtered and then mixed for 5 minutes in 6 ml of 50% solution of trifluoroacetic acid (TFA) in toluene (v/v) in temp. 60° C. with the use of external microwave radiation (power 20 W). The next step of the synthesis were three triple washings, for 1 minute each, with 6 ml portions of solvents: 3 times with DCM, 3 times with isopropyl alcohol (IPA) and again 3 times with DCM. Remains of TFA were neutralized in 10% solution of diisopropylethylamine (DIPEA) in N,N-dimethylformamide (DMF) (v/v) by stirring twice for 5 minutes each. Neutral pH was established through repetition of previous washings DCM, IPA, DCM (3 times for 1 minute each). Further the color Kaiser test was proceeded. For this purpose to test tube were added dropwise equal volumes (a few drops) of three solutions [(A): 5 g of ninhidrine in 100 ml of ethanol; (B): 80 g of phenol in 20 ml of ethanol; (C): 2 ml 0.001M aqueous KCN in 98 ml of pyridine], then small amount of resin beads was added and after that sample was warmed to 100° C. and left for 5 minutes. When positive result was achieved (navy blue color) the next step of synthesis was carried out, in which 38 mg (0.2 mmole) of Boc-Ala-OH, 64 mg (0.2 mmole) TBTU and 86 µl (0.5 mmole) DIPEA were dissolved in 5 ml of DMF. Obtained preactivation mixture was then added to the resin and stirred for 15 minutes in temp. 60° C. with external microwave radiation (power 20 W). After that resin was cooled, filtered and washed through with fresh portion (6 ml) of DCM for four times. Further the Kaiser test was proceeded (negative result—lack of color change). In the next step resin was stirred for 5 minutes with 6 ml of 50% TFA in toluene in temp. 60° C. with microwave radiation (power 20 W). The next step of the synthesis were three triple washings, for 1 minute each, with 6 ml portions of solvents: 3 times with DCM, 3 times with isopropyl alcohol (IPA) and again 3 times with DCM. Remains of TFA were neutralized in 10% solution of diisopropylethylamine (DIPEA) in N,N-dimethylformamide (DMF) (v/v) by stirring twice for 5 minutes each. Neutral pH was established through repetition of previous washings DCM, IPA, DCM (3 times for 1 minute each). In the next step the Kaiser test was proceeded and after positive result 69 mg (0.4 mmole) freshly synthesized Boc-Ala-H, dissolved in 5 ml of 1% acetic acid in DMF, was added to the resin and stirred for 3 minutes in temp. 80° C. with the use of microwave radiation (power 150 W). Further the solution was cooled and 25 mg (0.4 mmole) of $NaBH_3CN$ in 1 ml of DMF was added and stirring was continued for 6 minutes in 80° C. with the use of microwave radiation (power 150 W). After this time the resin was cooled, filtered and washed trough four times with 6 ml of DCM and again Kaiser test was proceeded. After that resin was filtered up and then was mixed for 5 minutes in 6 ml of 50% solution of trifluoroacetic acid (TFA) in toluene (v/v) in temp. 60° C. with the use of external microwave radiation (power 20 W). The next step of the synthesis were three triple washings, for 1 minute each, with 6 ml portions of solvents: 3 times with DCM, 3 times with isopropyl alcohol (IPA) and again 3 times with DCM. Remains of TFA were neutralized in 10% solution of diisopropylethylamine (DIPEA) in N,N-dimethylformamide (DMF) (v/v) by stirring twice for 5 minutes each. Neutral pH was established through repetition of previous washings DCM, IPA, DCM (3 times for 1 minute each). After obtaining a positive Kaiser test result the resin was supplemented with 3 ml solution of DMF containing 94 mg (0.2 mmole) of Boc-Lys(Fmoc)-OH, 64 mg (0.2 mmole) TBTU and 86 µl of DIPEA and the resin was stirred for 15 minutes in 60° C. with the use of microwave radiation (power 20 W). After this time the resin was cooled, filtered and washed trough four times with 6 ml of DCM and again Kaiser test was proceeded. After that resin was filtered up and then was mixed for 5 minutes in 6 ml of 50% solution of trifluoroacetic acid (TFA) in toluene (v/v) in temp. 60° C. with the use of external microwave radiation (power 20 W). The next step of the synthesis were three triple washings, for 1 minute each, with 6 ml portions of solvents: 3 times with DCM, 3 times with isopropyl alcohol (IPA) and again 3 times with DCM. Remains of TFA were neutralized in 10% solution of diisopropylethylamine (DIPEA) in N,N-dimethylformamide (DMF) (v/v) by stirring twice for 5 minutes each. Neutral pH was established through repetition of previous washings DCM, IPA, DCM (3 times for 1 minute each). After obtaining a positive Kaiser test result the resin was supplemented with 3 ml solution of DMF containing 94 mg (0.2 mmole) of Boc-Lys(Fmoc)-OH, 64 mg (0.2 mmole) TBTU and 86 µl of DIPEA and the resin was stirred for 15 minutes in 60° C. with the use of microwave radiation (power 20 W) After this time the resin was cooled, filtered and washed trough four times with 6 ml of DCM and again Kaiser test was proceeded. The next step was removal of Fmoc protecting group from side chain. For this purpose resin was stirred with 6 ml of 20% solution of piperidine in DMF for 5 minutes in 60° C. using microwave radiation (power 20 W). The next step of the synthesis were three triple washings, for 1 minute each, with 6 ml portions of solvents: 3 times with DCM, 3 times with isopropyl alcohol (IPA) and again 3 times with DCM and further Kaiser test. At the end of synthesis the reaction of guanidynylation was proceeded. For this purpose 100 mg (0.5 mmole) 1,5-dimethylpyrazole-1-carboxamidine nitrate (DMPCN) was dissolved in 5 ml of DMF and pH was shifted to 11 by the addition of DIPEA. Such prepared solution was added to the resin and stirred for 3 days. After that the resin was washed through with four portions of DMF and the Kaiser test was proceeded. Further the resin was prepared to product cleavage by washing through with DCM, methanol, diethyl ether (five times with each solvent) and dried in desiccator over NaOH. Full acidolytic raw compound cleavage from the resin support was achieved by stirring the resin in liquid HF with the addition of anisole as scavenger for 5 hours. Further the vessel was washed with diethyl ether and solid product was filtered on Schott's funnel. After that the peptide was dissolved in 50% aqueous acetic acid and lyophilized. The crude product was purified on semi-preparative high pressure liquid chromatography in reversed phase system on column with C-12 fill, using gradient method 0-15% (B) in 20 minutes, when (A): water+0.05% TFA; (B): acetonitrile+0.05% TFA.

Synthesis of Boc-Ala-H

In 10 ml of DCM stirred on magnetic stirrer a 190 mg (1.0 mmole) of Boc-Ala-OH and 353 mg (1.1 mmole) N-methyl, N-methoxyamine hydrochloride was added followed by 205 µl (1.2 mmole) DIPEA. The reaction was monitored by TLC using hexane:ethyl acetate (1:1 v/v). The reaction occurs in 1 hour and after this time the mixture was diluted with 20 ml of DCM, transferred to a separatory funnel and washed trough three times with 30 ml portions of 3M aqueous HCl, saturated $NaHCO_3$ and brine. The organic layer was dried over $MgSO_4$ and concentrated on rotary evaporator obtaining 186 mg (0.8 mmole) of product with a yield of 80%.

Further 186 mg (0.8 mmole) of the previous step's resulting Boc-Ala-N(OCH$_3$)CH$_3$ was dissolved in 20 ml of freshly distilled tetrahydrofuran (THF) over magnetic stirrer. The mixture was cool down in ice bath and the 123 mg (3.25 mmole) of powder $LiAlH_4$ was added portion wise. Reaction was monitored by TLC using hexane:ethyl acetate (1:1) and the reaction was completed in 30 minutes. After that a 442 mg (3.25 mmole) of $KHSO_4$ dissolved previously in 8 ml of water was added dropwise. The reaction mixture was then concentrated on rotary evaporator and the product was extracted three times with 20 ml portions of diethyl ether. The combined organic layers were washed with 30 ml portions of 3M aqueous HCl, saturated $NaHCO_3$ and brine. The organic layer was dried over $MgSO_4$ and concentrated on a rotary evaporator obtaining 90 mg (0.52 mmole) of Boc-Ala-H with a yield of 65%.

In an analogous way, one can obtain other compounds of the present invention belonging to this group.

EXAMPLE 4. EVALUATION OF THE BIOLOGICAL ACTIVITY OF COMPOUNDS ACCORDING TO THE PRESENT INVENTION—INHIBITORY PROPERTIES OF AGAINST THE VGEF$_{165}$/NRP-1 COMPLEX

Antiangiogenic properties were evaluated in vitro by measuring the inhibition of VEGF$_{165}$ to NRP-1 binding.

of the best hits, the compound concentration ranged from 0.01 to 300 μM. In the control wells, the tested compound was absent but the respective concentration of DMSO was maintained. The heptapeptide A7R (ATWLPPR) was routinely used as a positive control for each plate.

Results obtained for example peptidomimetics are shown in Table 2.

TABLE 2

Inhibition results obtained for example peptidomimetics

| | | % inhibition of VEGF165 to NRP-1 binding | | | | | | |
|---|---|---|---|---|---|---|---|---|
| Sequence | Name | 30 μM | 10 μM | 3 μM | 1 μM | 0.3 μM | 0.1 μM | 0.03 μM |
| AlaThrTrpLeuProProArg | A7R | 85.5 | 76.9 | 61.2 | | | | |
| Lys(hArg)-Pro-Dab-Arg | compound 2 | 100 | 98.3 | 93.6 | 82.6 | 62.2 | 35.4 | 13.7 |
| Lys(hArg)-Dap-Pro-Arg | compound 3 | 99.7 | 96.8 | 93.4 | 82.0 | 59.4 | 33.0 | 11.6 |
| Lys(hArg)-Dab-Pro-Arg | compound 4 | 100 | 98.5 | 91.4 | 82.4 | 47.8 | 21.6 | |

This test makes it possible to evaluate the % inhibition by the evaluated compound at a particular concentration. Novel compounds were decidedly better than the control peptide A7R and demonstrated inhibitory activity at concentrations in the order of nM.

Inhibitory Activity Determinations of the Evaluated Compounds.

The evaluation of the inhibitory effect of peptidomimetics were performed using an enzymatic method denoting the spectrophotometric displacement of the VEGF$_{165}$ ligand from a bond with the specific receptor Neuropilin-1 by the evaluated compound. The studies were performed using polystyrene 96-well plates (Maxisorb, Nunc.).

VEGF165 Displacement Assay

To evaluate the biological inhibitory activity of selected molecules, the surfaces of flat bottom polystyrene wells of 96-wells plates (Maxisorb, Nunc,) was treated with 100 ul of 2 ug/ml anti-Fc IgG (Sigma-Aldrich, Saint Quentin Fallavier, France) in phosphate buffer saline (PBS, Sigma) overnight at 4° C. After washing and saturation of non-specific interactions with bovine serum albumin (BSA, Sigma), purified recombinant rat NRP1-Fc (20 ng/well, R&D Systems, Abingdon, UK) in 50 μl PBS-BSA 0.1%-tween-80 0.005% (PBT), 50 μl of compound solution in PBT at final concentration of 100 μM and 50 μl of biotinylated VEGF165 (final concentration 1 nM, R&D Systems) diluted in PBT containing 2 μg/ml of heparin (Sigma) were successively added to a final volume of 150 μl. After an overnight incubation at 4° C., the wells were washed with PBT and treated with streptavidin-HRP polymer (Sigma) followed by washing and addition of ABTS substrate (Sigma). The DO measures were performed at 415 nm in reference to 470 nm after 15 minutes-2 h of reaction. To estimate the IC$_{50}$ and Ki

EXAMPLE 4. IN VITRO PEPTIDOMIMETIC STABILITY IN SERUM

The stability of two peptidomimetics: Lys(hArg)-Dap-Pro-Arg and Lys(hArg-Pro-Dab-Arg were tested in plasma samples obtained from healthy donors. Peptidomimetics stock solutions were prepared by dissolving the TFA salt of proper peptidomimetic in water to obtain a final peptidomimetic concentration of 0.7 μmol/mL. In a Eppendorf tube, samples of 100 μL of human plasma were temperature-equilibrated at 37° C. for 15 minutes before adding 100 μL of peptidomimetic stock solution. Three tubes allowed the analysis for each time point. The initial time was recorded and at known time intervals (every 10 minutes from 0 sec to 3 h), 400 μL of solution of TCA in 99.8% ethanol ($C_{TCA}$=0.2%) was added to the reaction solution for precipitation of the serum proteins. The cloudy reaction sample was shaken and then spun at 2000 g to pellet the precipitated serum proteins. The reaction supernatant was then analyzed by LC/MS analysis (using a RP-HPLC-ESI-MS system).

Our study showed that in the case of Lys(hArg)-Dap-Pro-Arg the main enzymatic cleavage occurs between the first and second residue, releasing Lys(hArg) and generating tripeptide Dap-Pro-Arg. The half-life time of Lys(hArg)-Dap-Pro-Arg was estimated to approximately 140 minutes. The second compound: Lys(hArg-Pro-Dab-Arg was degradated faster (to Lys(hArg)-Pro and Dab-Arg) and half-life time was estimated to 40 minutes. Therefore compound Lys(hArg)-Dap-Pro-Arg with half-life time approximately over 2 h (140 min) is stable enough to be the prospective antiangiogenic drug.

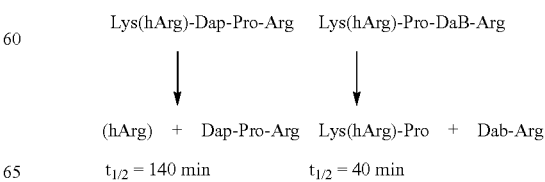

The invention claimed is:
1. A compound defined by the formula:

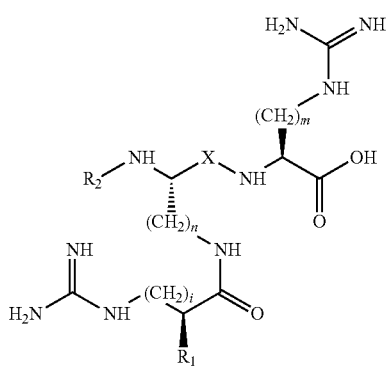

where:
i is an integer from 1 to 9,
n is an integer from 1 to 4,
m is an integer 3 or 4,
$R_1$ denotes: —H, —$NH_2$, —NH—CO—$CH_3$, —NH-Cbz, or —NH-Fmoc,
$R_2$ denotes: —H, —CO—$CH_3$, -Fmoc, or -Cbz,
X denotes one of the following molecular fragments from a) to e):

a)
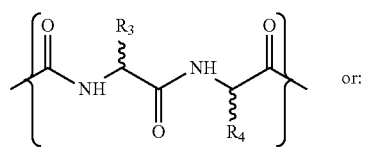
or:

b)
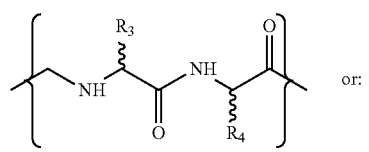
or:

c)
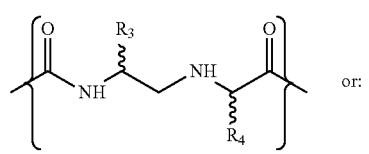
or:

d)
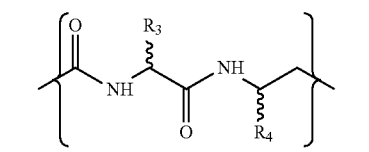

where:
$R_3$ and $R_4$ denote independently of one another a group selected from the side chains of: glycine, alanine, 2,3-diaminopropionic acid, 2,4-diaminobutanoic acid, ornithine, lysine, or proline connected to the carbon atom in an S or R configuration,
or:
e) —CO—NH—$(CH_2)_k$—CO—NH—, where k constitutes an integer in the range of 2-7, or its derivative containing a reduced peptide bond, or their pharmaceutically acceptable salts.

2. A compound according to claim 1, characterised in that it is a compound defined by the formula:

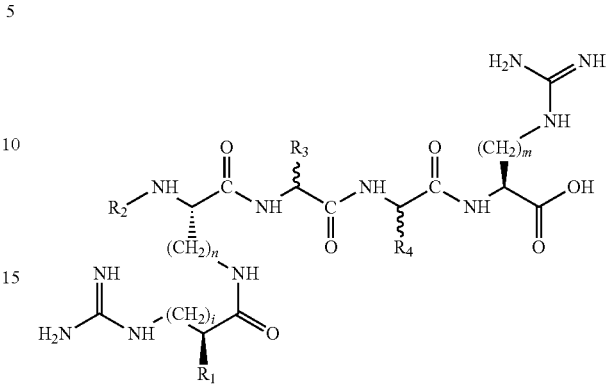

or its derivative containing a reduced peptide bond,
wherein i, n, m, $R_1$, $R_2$, $R_3$ and $R_4$ have the meaning defined in claim 1.

3. A compound according to claim 1, characterised in that it is a derivative containing a reduced peptide bond, wherein the reduction includes at least one of the peptide bonds denoted as A, B or C in the formula below:

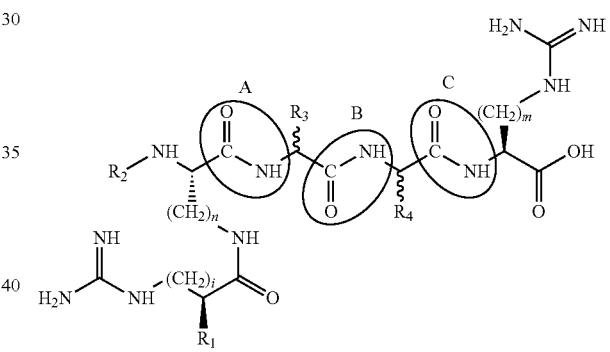

wherein i, n, m, $R_1$, $R_2$, $R_3$ and $R_4$ have the meaning defined in claim 1.

4. A compound according to claim 1, characterised in that it is a compound defined by the formula:

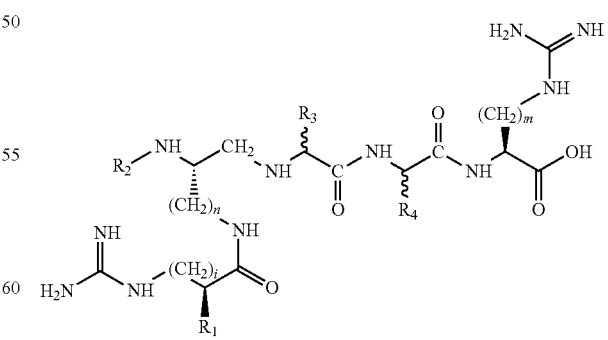

wherein i, n, m, $R_1$, $R_2$, $R_3$ and $R_4$ have the meaning defined in claim 1.

5. A compound according to claim 1, characterised in that it is a compound defined by the formula:

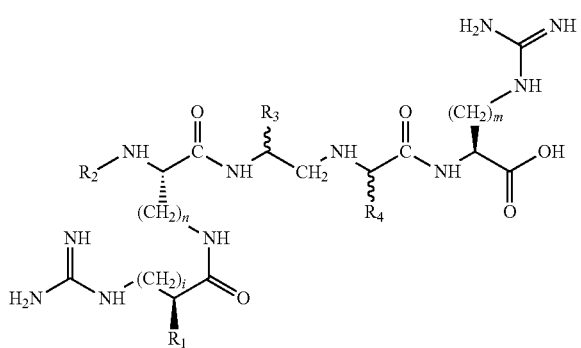

wherein i, n, m, $R_1$, $R_2$, $R_3$ and $R_4$ have the meaning defined in claim 1.

6. A compound according to claim 1, characterised in that it is a compound defined by the formula:

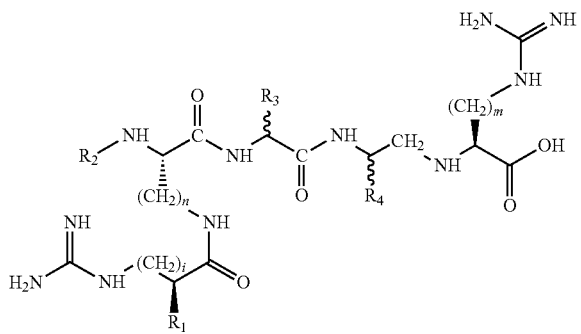

wherein i, n, m, $R_1$, $R_2$, $R_3$ and $R_4$ have the meaning defined in claim 1.

7. A compound according to claim 1, characterised in that is selected from a group consisting of:

Lys(hArg)-Pro-Dab-Arg,
Lys(hArg)-Dap-Pro-Arg,
Lys(hArg)-Dab-Pro-Arg,
Lys(hArg)-Ala-Ala-Arg,
Lys(hArg)-Ala-Pro-Arg,
Lys(hArg)-Pro-Ala-Arg,
Lys(11-Aun(g))-Pro-Dab-Arg,
Lys(7-Ahp(g))-Pro-Dab-Arg,
Lys(hArg)-Pro-Dap-Arg,
Lys(hArg)-Pro-Pro-Arg,
Lys(Dab(g))-Pro-Dab-Arg,
Dab(hArg)-Pro-Dab-Arg,
Orn(Arg)-Pro-Dab-Arg,
Orn(hArg)-Pro-Dab-Arg,
Lys(Arg)-Pro-Dab-Arg (SEQ ID NOs: 1-15 in order of appearance), or their pharmaceutically acceptable salts, wherein (g) denotes a guanidyl group, 11-Aun denotes 11-aminoundecanoic acid, and 7-Ahp denotes 7-aminoheptanoic acid residue.

8. A pharmaceutical composition, containing an active ingredient and a pharmaceutically permissible carrier, characterised in that it contains a compound defined in claim 1.

* * * * *

SEQUENCE LISTING

<160> NUMBER OF SEQ ID NOS: 16

<210> SEQ ID NO 1
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa stands for hArg
<220> FEATURE:
<221> NAME/KEY: MISC_FEATURE
<222> LOCATION: (4)..(4)
<223> OTHER INFORMATION: Xaa stands for Dab

<400> SEQUENCE: 1

Lys Xaa Pro Xaa Arg
1               5

<210> SEQ ID NO 2
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa stands for hArg
<220> FEATURE:
<221> NAME/KEY: MISC_FEATURE
<222> LOCATION: (3)..(3)
<223> OTHER INFORMATION: Xaa stands for Dap

<400> SEQUENCE: 2

Lys Xaa Xaa Pro Arg
1               5

<210> SEQ ID NO 3
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa stands for hArg
<220> FEATURE:
<221> NAME/KEY: MISC_FEATURE
<222> LOCATION: (3)..(3)
<223> OTHER INFORMATION: Xaa stands for Dab

<400> SEQUENCE: 3

Lys Xaa Xaa Pro Arg
1               5

<210> SEQ ID NO 4
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa stands for hArg

<400> SEQUENCE: 4

```
Lys Xaa Ala Ala Arg
1               5

<210> SEQ ID NO 5
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa stands for hArg

<400> SEQUENCE: 5

Lys Xaa Ala Pro Arg
1               5

<210> SEQ ID NO 6
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa stands for hArg

<400> SEQUENCE: 6

Lys Xaa Pro Ala Arg
1               5

<210> SEQ ID NO 7
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa stands for 11-Aun(g)
<220> FEATURE:
<221> NAME/KEY: MISC_FEATURE
<222> LOCATION: (4)..(4)
<223> OTHER INFORMATION: Xaa stands for Dab

<400> SEQUENCE: 7

Lys Xaa Pro Xaa Arg
1               5

<210> SEQ ID NO 8
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa stands for 7-Ahp(g)
<220> FEATURE:
<221> NAME/KEY: MISC_FEATURE
<222> LOCATION: (4)..(4)
<223> OTHER INFORMATION: Xaa stands for Dab

<400> SEQUENCE: 8

Lys Xaa Pro Xaa Arg
1               5
```

```
<210> SEQ ID NO 9
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa stands for hArg
<220> FEATURE:
<221> NAME/KEY: MISC_FEATURE
<222> LOCATION: (4)..(4)
<223> OTHER INFORMATION: Xaa stands for Dap

<400> SEQUENCE: 9

Lys Xaa Pro Xaa Arg
1               5

<210> SEQ ID NO 10
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa stands for hArg

<400> SEQUENCE: 10

Lys Xaa Pro Pro Arg
1               5

<210> SEQ ID NO 11
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa stands for Dab(g)
<220> FEATURE:
<221> NAME/KEY: MISC_FEATURE
<222> LOCATION: (4)..(4)
<223> OTHER INFORMATION: Xaa stands for Dab

<400> SEQUENCE: 11

Lys Xaa Pro Xaa Arg
1               5

<210> SEQ ID NO 12
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa stands for Dab
<220> FEATURE:
<221> NAME/KEY: MISC_FEATURE
<222> LOCATION: (2)..(2)
<223> OTHER INFORMATION: Xaa stands for hArg
<220> FEATURE:
<221> NAME/KEY: MISC_FEATURE
<222> LOCATION: (4)..(4)
<223> OTHER INFORMATION: Xaa stands for Dab
```

```
<400> SEQUENCE: 12

Xaa Xaa Pro Xaa Arg
1               5

<210> SEQ ID NO 13
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa stands for Orn
<220> FEATURE:
<221> NAME/KEY: MISC_FEATURE
<222> LOCATION: (4)..(4)
<223> OTHER INFORMATION: Xaa stands for Dab

<400> SEQUENCE: 13

Xaa Arg Pro Xaa Arg
1               5

<210> SEQ ID NO 14
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa stands for Orn
<220> FEATURE:
<221> NAME/KEY: MISC_FEATURE
<222> LOCATION: (4)..(4)
<223> OTHER INFORMATION: Xaa stands for Dab

<400> SEQUENCE: 14

Xaa Arg Pro Xaa Arg
1               5

<210> SEQ ID NO 15
<211> LENGTH: 5
<212> TYPE: PRT
<213> ORGANISM: artificial
<220> FEATURE:
<223> OTHER INFORMATION: Synthesized
<220> FEATURE:
<221> NAME/KEY: MISC_FEATURE
<222> LOCATION: (4)..(4)
<223> OTHER INFORMATION: Xaa stands for Dab

<400> SEQUENCE: 15

Lys Arg Pro Xaa Arg
1               5

<210> SEQ ID NO 16
<211> LENGTH: 7
<212> TYPE: PRT
<213> ORGANISM: artificial
<220> FEATURE:
<223> OTHER INFORMATION: Synthesized

<400> SEQUENCE: 16

Ala Thr Trp Leu Pro Pro Arg
1               5
```